United States Patent
Wang et al.

(10) Patent No.: US 9,856,285 B2
(45) Date of Patent: Jan. 2, 2018

(54) REAGENTS FOR UNIVERSAL SITE-SPECIFIC LABELING AND MODIFICATIONS OF NUCLEIC ACIDS

(71) Applicant: KAOHSIUNG MEDICAL UNIVERSITY, Kaohsiung (TW)

(72) Inventors: Tzu-Pin Wang, Tainan (TW); Yu-Chih Su, Tainan (TW)

(73) Assignee: KAOHSIUNG MEDICAL UNIVERSITY (TW)

( * ) Notice: Subject to any disclaimer, the term of this patent is extended or adjusted under 35 U.S.C. 154(b) by 161 days.

(21) Appl. No.: 14/660,489

(22) Filed: Mar. 17, 2015

(65) Prior Publication Data

US 2016/0272669 A1    Sep. 22, 2016

(51) Int. Cl.
| C07H 21/02 | (2006.01) |
| C07H 21/04 | (2006.01) |
| C07H 21/00 | (2006.01) |
| C07K 1/00  | (2006.01) |
| C07K 14/00 | (2006.01) |
| C07K 17/00 | (2006.01) |
| C07H 1/00  | (2006.01) |

(52) U.S. Cl.
CPC ............ C07H 21/02 (2013.01); C07H 1/00 (2013.01); C07H 21/04 (2013.01)

(58) Field of Classification Search
CPC ........ C07H 21/02; C07H 21/04; G01N 33/60; G01N 33/582
See application file for complete search history.

(56) References Cited

U.S. PATENT DOCUMENTS

| 6,664,079 B2 * | 12/2003 | Ju | ........................ C12Q 1/686 435/6.1 |
| 7,345,159 B2 * | 3/2008  | Ju | ........................ C12Q 1/686 435/6.1 |
| 7,635,578 B2 * | 12/2009 | Ju | ........................ C12Q 1/686 435/6.11 |
| 7,713,698 B2 * | 5/2010  | Ju | ........................ C12Q 1/686 435/6.14 |
| 7,790,869 B2 * | 9/2010  | Ju | ........................ C12Q 1/686 435/6.11 |
| 8,088,575 B2 * | 1/2012  | Ju | ........................ C12Q 1/686 435/6.12 |
| 9,133,511 B2 * | 9/2015  | Ju | ........................ C12Q 1/686 |

OTHER PUBLICATIONS ( R ) Rostovtsev et al., "A Stepwise Huisgen Cycloaddition Process: Copper(I)-Catalyzed Regioselective "Ligation" of Azides and Terminal Alkynes," Angew. Chem. Intl . Ed., 41(14), 2596-2599 (2002.*
(S) Agard et al., A Strain Promoted [3+2] Azide-Alkyne Cycloaddition for Covalent Modification of Biomolecules in Living Systems, Journal of the American Chemical Society, 126 (46), 15046-15047 (Nov. 2, 2004).*

Grandjean et al. "On the Preparation of Carbohydrate-Protein Conjugates Using the Traceless Staudinger Ligation", J. Org. Chem. vol. 70, pp. 7123-7132 (2005).
Hong, Vu et al. "Analysis and Optimization of Copper-Catalyzed Azide-Alkyne Cycloaddition for Bioconjugation", Angew Chem Int Ed Engl. 48(52), pp. 9879-9883 (2009).
Leonard, Nicholas M. et al. "In Situ Formation of N-trifluoroacetoxy Succinimide (TFA-NHS): One-Pot Formation of Succinimidyl Esters, N-Trifluoroacetyl Amino Acid Succinimidyl Esters, and N-Maleoyl Amino Acid Succinimidyl Esters", J. Org. Chem. vol. 76, pp. 9169-9174 (2011).
Poole, Leslie B. et al. "Fluorescent and Affinity-Based Tools to Detect Cysteine Sulfenic Acid Formation in Proteins", Bioconjugate Chem. vol. 18, pp. 2004-2017 (2007).
Seo, Tae Seok et al. "Click Chemistry to Construct Fluorescent Oligonucleotides for DNA Sequencing", J. Org. Chem. vol. 68, pp. 609-612 (2003).

(Continued)

Primary Examiner — Lawrence E Crane
(74) Attorney, Agent, or Firm — Volpe and Koenig, P.C.

(57) ABSTRACT

The present invention discloses a method of harnessing versatile phosphoramidation reactions to regioselectively link a group of alkynyl-/azido-containing compounds to post-synthetic nucleic acids primed with phosphate at the 5' termini. The method includes steps of: (a) monophosphoramidating $H_2N(CH_2)_nNH_2$ to the 5' end of the nucleic acid to form an intermediate 1 where n is an integer from 2 to 6, and the intermediate 1 has a formula of:

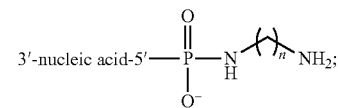

(b) amidating the free —$NH_2$ group of the intermediate 1 with

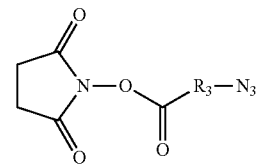

to form an intermediate 2; and (c) reacting the terminal —$N_3$ group of the intermediate 2 with 1-{3-{[4-(2-cyclooctyn-1-ylmethyl)benzoyl]amino}propyl}-4-{2-[4-(dimethylamino)phenyl]ethenyl}pyridinium hexafluorophosphate (Alkyne MegaStokes dye 608) by the SPAAC reaction to form modified nucleic acids. Without the presence of Cu(I), the modified nucleic acids were subjected to azide-alkyne cycloaddition in an aqueous solution to obtain various nucleic acid conjugates with a high yield.

3 Claims, 5 Drawing Sheets
(1 of 5 Drawing Sheet(s) Filed in Color)

(56) References Cited

OTHER PUBLICATIONS

Su, Yu-Chi H et al. "Azide-Alkyne Cycloaddition for universal post-synthetic modifications of nucleic acids and effective synthesis of bioactive nucleic acid conjugates", Org. Biomol. Chem. vol. 12, pp. 6624-6633 (2014).
Wang, Tzu-Pin et al. "Advanced Aqueous-Phase Phosphoramidation Reactions for Effectively Synthesizing Peptide-Oligonucleotide Conjugates Trafficked into a Human Cell Line", Bioconjugate Chem. vol. 23, pp. 2417-2433 (2012).
Winz, Marie-Luise et al. "Site-specific terminal and internal labeling of RNA by poly(A) polymerase tailing and copper-catalyzed or copper-free strain-promoted click chemistry", Nucleic Acids Research vol. 40, No. 10, 13 pages (2012).

\* cited by examiner

REAGENTS FOR UNIVERSAL SITE-SPECIFIC LABELING AND MODIFICATIONS OF NUCLEIC ACIDS

FIELD OF THE INVENTION

The present invention relates to a new coupling method for the post-synthetic modification of nucleic acids by combining aqueous-phase two-step phosphoramidation reactions and azide-alkyne cycloaddition reactions.

BACKGROUND OF THE INVENTION

Extensive research has been devoted to exploring the therapeutic potential of nucleic acids, including small interfering (siRNA), microRNA (miRNA), catalytic RNA (ribozymes), aptamer oligonucleotides (oligonucleotides with exquisite roles similar to protein receptors), and antisense oligonucleotides. Theoretically, when designed appropriately, nucleic acids delivered into biological systems will participate in cellular activities, such as RNA interference or gene silencing, to abolish specific gene expression in cells and to attain more precise therapeutic targeting than typical small molecule drugs. Nucleic acid-based therapeutics have shown promise for treating a variety of human genetic diseases and microbial infections. Recent progress has resulted in some antisense oligonucleotides and aptamer RNA reaching clinical applications, while a significant number of clinical trials for siRNA are underway.

The direct use of nucleic acids for treating diseases, however, faces serious hurdles. Difficulties include cell specificity, inefficient cellular uptake of nucleic acids, and inaccessibility of nucleic acids to cell nuclei, due primarily to ineffective translocation of nucleic acids across biological barriers after administration. Consequently, successful use of nucleic acids in clinical practice will not be achieved until there are better strategies for targeted and efficient delivery of nucleic acids to cells and tissues. The critical issue of efficient target delivery for nucleic acids has been studied by many laboratories through chemical modification of nucleic acids to improve stability and cellular delivery properties of nucleic acids in vivo.

Developed methods include conjugating cellular surface receptor-specific ligands with various nucleic acid-containing nanocarriers or covalently linking cellular surface receptor-specific ligands with nucleic acids directly.

The use of peptides as ligands to traffic nucleic acids across the plasma membrane has been extensively investigated in the development of effective nucleic acid-based therapeutic agents. Conjugating nucleic acids such as oligonucleotides with cell-penetrating peptides (CPPs) or cell-targeting peptides (CTPs) to acquire peptide-oligonucleotide conjugates (POCs) has created appropriate designs to circumvent cellular delivery or cell specificity problems inherited from administrating only oligonucleotides in clinics. CPPs, including the Tat, the Antennapedia, the CyLoP-1 (a cysteine-rich CPP), and the $(KFF)_3K$ peptides, are either protein-derived or artificially developed short sequences (10-16 amino acids), and they are able to spontaneously cross cellular barriers when provided in extracellular media. The unique cell permeability properties of CPPs significantly improve the uptake efficiency of oligonucleotides in POCs by cells and facilitate broader uses of POCs in science and medicine.

POCs are primarily prepared by coupling peptides with oligonucleotides after solid-phase synthesis (fragment coupling strategy) or directly synthesized through stepwise solid-phase reactions (online solid-phase synthesis). To achieve peptide-oligonucleotide conjugations, current POC synthesis methods typically require previous incorporations of additional functionalities in peptides, oligonucleotides, or both. The requirement to have additional functional groups renders these methods inefficient, inconvenient, and not cost-effective for academia or industry. The development of a facile approach to exploit readily available functionalities, such as hydroxyl or phosphate groups, in standard oligonucleotides in order to synthesize POCs with high purity and yields is crucial to the advancement of POC applications.

Regioselective modifications of biomolecules with tags, probes or other biological molecules have been a critical tool which significantly advanced biomolecular studies for fundamental research and clinical application. In nucleic acids, site-specific modifications of smaller DNA/RNA such as oligonucleotides can be achieved through phosphoramidite chemistry to link predefined chemical moieties to positions in specific nucleotides during solid-phase oligonucleotide synthesis. However, the solid-phase chemistry approach for regioselective modifications of oligonucleotides suffers from inherited drawbacks including limits on the length of synthesized oligonucleotides and on the variety of their incorporated chemical functionality.

To complement the shortcomings of solid-phase oligonucleotide synthesis, many site-specific post-synthetic modification methods for nucleic acids have been studied and adapted to any size of nucleic acid and a broad diversity of chemical groups integrated into the nucleic acids. Nevertheless, recently developed post-synthetic modification methods for nucleic acids rely on enzyme catalysis to carry out chemical transformations but are unable to provide a universal strategy for both DNA and RNA modifications. Moreover, the required expensive enzymes and specific substrates in enzymatic reactions further stymie the efforts to modify nucleic acids with various chemical entities within reasonable costs.

SUMMARY OF THE INVENTION

To overcome the deficiencies in the prior arts, the present invention discloses a facile universal, economical approach by harnessing versatile aqueous-phase two-step phosphoramidation reactions to regioselectively incorporate alkynyl/azido groups into post-synthetic nucleic acids primed with phosphate at the 5' termini.

This post-synthetic modification method for nucleic acids is made possible by orthogonal azide-alkyne cycloaddition reactions. The powerful copper-catalyzed azide-alkyne cycloaddition (CuAAC) reaction, a prototype of click chemistry, has found broad applications in science ranging from material studies to biomolecular research. In addition, the copper-free variant of the CuAAC reaction, strain-promoted azide-alkyne cycloaddition (SPAAC), harnesses excellent reactivity of cyclooctyne derivatives and dramatically expands the biocompatibility of the 1,3-dipolar cycloaddition reaction for studying biomolecules in vivo.

The aqueous-phase two-step phosphoramidation reactions are an ideal strategy to synthesize POCs without compromising oligonucleotide base-pairing specificity, an essential criterion when administrating oligonucleotides as therapeutic agents. This facilitates the introduction of azido and alkynyl groups to DNA/RNA. The acquired azide- and alkyne-modified nucleic acids set the stage for azide-alkyne cycloaddition and allow effective and efficient conjugations with derivatives of biotin, fluorescein, and a CPP the Tat peptide. As proof of the concept, the inventors further demonstrated that the CuAAC-synthesized POC was bioavailable and successfully trafficked into human cells.

BRIEF DESCRIPTION OF THE DRAWINGS

The patent or application file contains at least one drawing executed in color. Copies of this patent or patent application publication with color drawing will be provided by the Office upon request and payment of the necessary fee.

FIGS. 2(A) and 2(B) are gel electrophoretic results showing azide-alkyne cycloaddition for the $^{32}$P-labeled alkyne-modified (A) 3' primer DNA and (B) 17-mer RNA with azido-containing substrates. Lanes in FIG. 2(A): 1, ethylenediamine; 9, ethylenediamine+19; and 10, ethylenediamine+19+16. Lanes in FIG. 2(B): 6, cystamine; 11, cystamine+19; and 12, cystamine+19+12. Labels in FIG. 2(A): e, the 3' primer DNA-ethylenediamine conjugate; f, the 3' primer DNA; k, the alkynyl 3' primer DNA-16 conjugate prepared by the CuAAC reaction; and l, the 3' primer DNA-ethylenediamine-19 conjugate. Labels in FIG. 2(B): h, the 17-mer RNA-cystamine-6c conjugate; j, the 17-mer RNA; m, the streptavidin (SAv)-shifted alkynyl 17-mer RNA-12 conjugate prepared by the CuAAC reaction; n, the alkynyl 17-mer RNA-12 conjugate prepared by the CuAAC reaction; and o, the 17-mer RNA-cystamine-19 conjugate. It is to be noted that the area between the wavy lines in FIG. 2(B) has been cut off from the original scan because it contains no detectable signals.

DETAILED DESCRIPTION OF THE PREFERRED EMBODIMENTS

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed.

In order to accomplish the purpose of the present invention, the technical schemes of the present invention are specifically described as follows.

The present invention discloses the aqueous-phase two-step phosphoramidation reaction-based modifications of nucleic acids with azides and alkynes for subsequent synthesis of nucleic acid conjugates including POCs by the CuAAC and SPAAC reactions.

In a first preferred embodiment of the present invention, a method for modifying an oligonucleotide by the CuAAC or SPAAC reaction with azide-modified oligonucleotides is disclosed as follows and includes steps of:
(a) conjugating $H_2N(CH_2)_nNH_2$ to the 5' end of the oligonucleotide (i.e. an reactant 1) to form an intermediate 1 where n is an integer from 2 to 6;
(b) amidating the free —$NH_2$ group of the intermediate 1 with to form an intermediate 2; and
(c) reacting the terminal —$N_3$ group of the intermediate 2 with one of HC≡C—$R_2$ by the CuAAC reaction and 1-{3-{[4-(2-cyclooctyn-1-ylmethyl)benzoyl] amino}propyl}-4-{2-[4-(dimethylamino)phenyl] ethenyl}pyridinium hexafluorophosphate (Alkyne MegaStokes dye 608) by the SPAAC reaction to form a product 1 and a product 2, respectively.

reactant 1

$R^3$, substituents in azides; $R^4$, substituents in alkyne; n is an integer from 2 to 6

The step (a) is called the aqueous-phase two-step phosphoramidation reaction.

In a second preferred embodiment of the present invention, a method for modifying an oligonucleotide by the CuAAC reaction with alkyne-modified oligonucleotides is disclosed as follows and includes steps of:
(a) conjugating $H_2N(CH_2)_nNH_2$ to the 5' end of the oligonucleotide (i.e. the reactant 1) to form the intermediate 1 where n is an integer from 2 to 6;
(b) amidating a free —$NH_2$ group with to form an intermediate 3; and
(c) reacting the alkyne group of the intermediate 3 with $R^6$—$N_3$ by the CuAAC reaction to form a product 3.

$R^6$, substituents in azides; $R^5$, substituents in alkynes; n is an integer from 2 to 6

The step (a) above is called the aqueous-phase two-step phosphoramidation reaction.

In a third preferred embodiment of the present invention, a method for modifying an nucleic acid by the CuAAC reaction with azide-modified nucleic acids for synthesis of POCs is disclosed as follows and includes steps of:
(a) conjugating $H_2NCH_2CH_2NH_2$ to the 5' end of the nucleic acid (i.e. the reactant 1) to form an intermediate 4;

(b) amidating a free —NH₂ group of the intermediate 4 with to form an intermediate 5 where m=4; and
(c) reacting the alkyne group of the intermediate 5 with a molecule having a structure of CH≡C-Tat peptide by the CuAAC reaction to form a product 4 (a type of POCs).

The step (a) above is called the aqueous-phase two-step phosphoramidation reaction.

In order to accomplish the purposes of the present invention, the materials and methods are described as follows. The following Examples illustrate the invention and are not to be construed as limitations of the invention.

General Materials and Methods

The standard Tat peptide (being the 48$^{th}$ to 57$^{th}$ amino acid residues in the Tat protein and having the sequence in H₂N-GRKKRRQRRR-COOH (SEQ ID NO. 1); each bold and capitalized letter standing for a specific amino acid residue) and its alkynyl version (amidation with 5-hexynoic acid at the N terminus of the Tat peptide) were purchased from Peptide 2.0 (Chantilly, Va., USA).

$^{1}$H and $^{13}$C nuclear magnetic resonance (NMR) spectra were recorded using either a Varian 200 or 400 MHz spectrometer (Varian, Inc., Palo Alto, Calif., USA). NMR samples were prepared in CD₃OD, D₂O or CDCl₃, and the chemical shifts of $^{1}$H signals were given in parts per million downfield from tetramethylsilane (TMS). $^{13}$C signals were given in parts per million based on the internal standard of each deuteriated solvent. Electrospray ionization (ESI) high resolution mass spectra were acquired on a Bruker APEX II Fourier-transfer mass spectrometer (FT-MS; Bruker Daltonics Inc., Taiwan). Inductively coupled plasma-mass spectrometer (ICP-MS) analysis for quantification of copper in POCs was also performed on a PE-SCIEX ELAN 6100 DRC mass spectrometer (PerkinElmer Taiwan, Kaohsiung, Taiwan). Radio-labeled or biotin-/fluorophore-modified nucleic acid conjugates were analyzed by urea polyacrylamide gel electrophoresis (urea-PAGE) or SAv gel shift assay in urea-PAGE, visualized and quantified by an Amersham Typhoon PhosphorImager (GE Healthcare Bio-Sciences AB, Uppsala, Sweden). The molecular mass of purified nucleic acid conjugates was determined by an Autoflex III TOF/TOF analyzer (Bruker Daltonics). POC uptake by human A549 cells was analyzed by a BD FACSCalibur cytometer (BD, Franklin Lakes, N.J., USA) and a FluoView 1000 confocal laser scanning microscope (Olympus, Tokyo, Japan).

EXAMPLE 1

Optimization of Two-Step Nucleic Acid Phosphoramidation Reactions.

The optimized two-step phosphoramidation reaction for RNA was carried out by dissolving the guanosine monophosphate (GMP)-primed TW17 RNA (SEQ ID NO: 2, 87-mer; 5'-GGGAUCGUCAGUGCAUUGAGAAGUGCA-GUGUCUUGCGCUGGGU UCGAGCGGUCCGUG-GUGCUGGCCCGGUGGUAUCCCCAAGGGGU A-3') (0.32 nmol) and 1-(3-dimethylaminopropyl)-3-ethylcarbodiimide hydrochloride (EDC, 4.17 μmol) in 4 μL 4(5)-methylimidazole-Triton X-100 buffer [0.1 M 4(5)-methylimidazole, 15% Triton X-100, pH 6.0] and activating at room temperature (rt) for 90 min. The resulting 5'-phosphorimidazolide RNA was purified by ethanol precipitation and resuspended in 5.5 μL of EPPS-Triton X-100 buffer (100 mM EPPS, 15% Triton X-100, 2 mM EDTA, pH 7.5). One microliter of compound 1 [187.2 mM in dimethylformamide (DMF)] was then added to the 5'-phosphorimidazolide RNA solution to allow a phosphoramidation reaction at 41° C. for 3 h.

Compound 1

For single-stranded DNA, the optimized two step phosphoramidation reaction was performed by dissolving the single-stranded DNA (0.32 nmol) and EDC (4.17 μmol) in 4 μL of 4(5)-methylimidazole buffer [0.1 M 4(5)-methylimidazole, pH 6.0] and activating at rt for 90 min. Similarly, the resulting 5'-phosphorimidazolide DNA was purified by ethanol precipitation and redissolved in 5.5 μL of EPPS buffer (100 mM EPPS, 2 mM EDTA, pH 7.5). A solution of compound 1 (1 μL; 187.2 mM in DMF) was later added to the 5'-phosphorimidazolide DNA solution to allow a phosphoramidation reaction at 55° C. for 3 h. No co-solute was used in the two-step phosphoramidation reaction of the single-stranded DNA to attain a higher reaction yield. All of the resulting nucleic acid-substrate conjugates were purified twice by ethanol precipitation, analyzed by urea-PAGE and SAv gel shift assay (8% urea-PAGE for the TW17 RNA, and 20% urea-PAGE for the single-stranded 3'-primer DNA), visualized, and quantified by an Amersham Typhoon PhosphorImager to determine the reaction yield.

EXAMPLE 2

Two-Step Phosphoramidation Reactions for Synthesis of Nucleic Acid-Tat$_{48-57}$ Peptide Conjugates.

The single-stranded 3'-primer DNA was conjugated with the Tat$_{48-57}$ peptide according to the optimized two-step phosphoramidation reaction described previously but with the following modifications. First, the scale of the reaction was increased five times to acquire sufficient conjugates for the subsequent ex vivo studies. In addition, the pH of the conjugation reaction between the 5'-phosphorimidazolide DNA and the Tat$_{48-57}$ peptide was increased to 8.0 achieved by the addition of concentrated EPPS buffer (600 mM EPPS, 5 mM EDTA, pH 8.0) to attain a higher yield. Finally, only 20 mM of the Tat$_{48-57}$ peptide was required in the coupling reaction to generate the best yield.

For RNA-Tat$_{48-57}$ conjugates, preparation also followed the optimized two-step RNA phosphoramidation reaction but with the following modifications: (1) Only 20 mM of the Tat$_{48-57}$ peptide was required in conjugation reactions, and (2) concentrated EPPS-Triton X-100 buffer (600 mM EPPS, 15% Triton X-100, 5 mM EDTA, pH 7.5) was added to the conjugation reaction between the 5'-phosphorimidazolide RNA and the Tat$_{48-57}$ peptide to retain the buffering capacity.

The synthesized nucleic acid-Tat$_{48-57}$ conjugates were also purified twice by ethanol precipitation, analyzed by 8% (the TW17 RNA) or 20% (the 3' primer DNA and the TW17$_{1-17}$ RNA) urea-PAGE, visualized and quantified by an Amersham Typhoon PhosphorImager.

EXAMPLE 3

Two-Step Phosphoramidation Reactions for Synthesis of Nucleic Acid-Cystamine Conjugates.

Similar optimized two-step phosphoramidation reactions were applied when preparing nucleic acid-cystamine conjugates and are described below. The RNA-cystamine conjugate synthesis was carried out by dissolving the GMP-primed TW17$_{1-17}$ RNA (0.32 nmol) and EDC (4.17 μmol) in 4 μL of 4(5)-methylimidazole-Triton X-100 buffer and activating at rt for 90 min. The resulting 5'-phosphorimidazolide RNA was purified by ethanol precipitation and then resuspended in 5.5 μL of concentrated EPPS-Triton X-100 buffer with the addition of 1 μL of cystamine (187.2 mM in water) to allow a reaction at 41° C. for 3 h.

For the single-stranded 3'-primer DNA, the cystamine conjugate was prepared by dissolving the DNA (1.59 nmol) and EDC (26 μmol) in 20 μL 4(5)-methylimidazole buffer and activating at rt for 90 min. The resulting 5'-phosphorimidazolide DNA was purified by ethanol precipitation, redissolved in 27.5 μL of concentrated EPPS buffer. Five microliters of cystamine (187.2 mM in DEPC water) was then added to the 5'-phosphorimidazolide DNA solution to allow a reaction at 55° C. for 3 h. Again, no co-solute was used in the two-step phosphoramidation reaction of the single-stranded DNA to attain a higher reaction yield.

The products of the conjugation reactions between cystamine and nucleic acids (the 3' primer DNA and the TW17$_{1-17}$ RNA) were separated by 20% urea-PAGE, visualized and quantified by an Amersham Typhoon PhosphorImager to determine reaction yield.

EXAMPLE 4

Synthesis of Azido Carboxylic Acid Succinimidyl Esters (6)

Synthesis of 6a and its precursor 3-azidopropionic acid (5a) from 3-bromopropionic acid (4a), and synthesis of 6b from 4-bromobutyric acid (4b) were achieved by following the procedures of Grandjean et al. (C. Grandjean et al., *J. Org. Chem.*, 2005, 70, 7123-7132). The synthesis of 6c generally adhered to the method of Seo et al. (T. S. Seo et al., *J. Org. Chem.*, 2003, 68, 609-612).

Synthesis of 6-azido-hexanoic acid 2,5-dioxo-pyrrolidin-1-yl ester (6d)

Synthesis of 6d was achieved by modifying a published method (N. M. Leonard et al., *J. Org. Chem.*, 2011, 76, 9169-9174) as briefly described below. First, the required 6-azidohexanoic acid (5d) was synthesized by dissolving and reacting 6-bromohexanoic acid (4d; 3.0 g, 15.4 mmol) with sodium azide (2.0 g, 30.8 mmol) in DMF (10 mL) at 85° C. for 3 h. The resulting reaction mixture was diluted with dichloromethane (DCM), extracted with 0.1 N HCl, dried over $Na_2SO_4$, and concentrated under reduced pressure to obtain the colorless oil of 5d (80%).

Without further purification, the acquired 5d (1.352 g, 8.8 mmol) was dissolved and stirred in a DMF solution (20 mL) and submerged in an ice-water bath, followed by the slow addition of sym-collidine (2.5 mL, 18.5 mmol) in 10 min to obtain the Flask A solution. Immediately, the Flask B solution was prepared by dissolving N-hydroxysuccinimide (NHS, 4.048 g, 35.2 mmol) in the other DMF solution (20 mL) also immersed in an ice-water bath, followed by the slow addition of trifluoroacetic anhydride (TFAA, 4.93 mL, 35.2 mmol) while stirring for 10 min, and finally dropwisely adding sym-collidine (4.66 mL, 34.5 mmol) in 10 min to obtain the solution. The Flask B solution was then slowly dripped into the Flask A solution in 1.5 h while maintaining both solutions at 0° C. The resulting mixture was returned to rt and stirred overnight. The final reaction mixture was diluted with DCM (60 mL), extracted with 1 N HCl (50 mL) three times, dried over $Na_2SO_4$, concentrated under reduced pressure, and further washed with $Et_2O$ (40 mL) three times to obtain the white-colored solid 6d (2.14 g, 76%).

Compound 6d: $^1$H NMR (400 MHz) ($CDCl_3$) δ: 3.30 (t, 2H), 2.84 (br s, 4H), 2.64 (t, 2H), 1.79 (q, 2H), 1.68-1.60 (m, 2H), 1.55-1.48 (m, 2H). $^{13}$C NMR (100.67 MHz) ($CDCl_3$) δ: 169.1, 168.4, 51.0, 30.7, 28.3, 25.8, 25.5, 24.1. HRMS (ESI) calculated for $C_{10}H_{14}N_4O_4$, $[M+Na]^+$ 277.09073 (calculated), 277.09081 (found).

Synthesis of 2'-aminoethyl 5-azido-pentanamide, TFA salt (7)

A reaction mixture for compound 7 synthesis was prepared by dissolving 6c (0.29 g, 1.2 mmol) in DCM (2 mL) first followed by the addition of $Et_3N$ (0.16 mL, 1.16 mmol) and mono-t-Boc-ethylenediamine (0.24 g, 1.5 mmol) to the DCM solution. After reacting at rt for 7 h, the final reaction mixture was diluted with DCM, and extracted with 1 N HCl, 5% $NaHCO_3$ and saturated NaCl, sequentially. The resulting organic phase was dried over $Na_2SO_4$ and concentrated under reduced pressure to obtain the Boc-protected 7 which was deprotected by dissolving in 1 mL of TFA while stirring at 0° C. for 1 h, removed TFA under reduced pressure, washed with $Et_2O$ to obtain the colorless oil-like compound 7 (0.17 g, 75%).

Compound 7: $^1$H NMR (400 MHz) ($CDCl_3$) δ: 3.32 (t, 2H), 2.41 (t, 2H), 1.78-1.60 (m, 4H). $^{13}$C NMR (100.67 MHz) ($CDCl_3$) δ: 178.1, 51.0, 33.2, 28.3, 28.2, 21.8. HRMS (ESI) calculated for $C_7H_{16}N_5O$, $[M+H]^+$ 186.13494 (calculated), 186.13490 (found).

EXAMPLE 5

Synthesis of Biotin Derivatives, 10 and 12
5-(2-Oxo-hexahydro-thieno[3,4-d]imidazol-4-yl)-pentanoic acid prop-2-ynylamide (10)

The method of Poole et al. (L. B. Poole et al., *Bioconjugate Chem.*, 2007, 18, 2004-2017) was adopted to synthesize 10.

5-(2-Oxo-hexahydro-thieno[3,4-d]imidazol-4-yl)-pentanoic acid [2-(5-azido-pentanoylamino)-ethyl]-amide (12)

The reaction mixture for 12 synthesis was prepared by dissolving 7 (0.098 g, 0.58 mmol), $Et_3N$ (82 μL, 0.58 mmol) and (+)-biotin N-hydroxysuccinimide ester [11; 0.19 g, 0.55 mmol; synthesized from (+)-biotin (8)] in 5 mL of DMF while stirring at rt for 5 h. The final reaction mixture was concentrated under reduced pressure, recrystallized in isopropyl alcohol (IPA), and washed with ethyl acetate (EA) to obtain the white-colored solid 12 (0.371 g, 80%).

Compound 12: $^1$H NMR (400 MHz) (CD$_3$OD) δ: 4.49 (1H, dd), 4.31 (1H, dd), 2.93 (1H, dd), 2.70 (1H, d), 1.60-1.31 (4H, m), 1.25 (2H, q). $^{13}$C NMR (100.67 MHz) (CD$_3$OD) δ: 176.4, 176.1, 63.4, 61.6, 57.0, 52.1, 47.9, 41.0, 40.1, 36.8, 36.5, 29.8, 29.5, 29.4, 26.8, 24.1. HRMS (ESI) calculated for C$_{17}$H$_{29}$N$_7$O$_3$, [M+Na]$^+$ 434.1950 (calculated), 434.1947 (found).

EXAMPLE 6

Synthesis of Fluorescein Derivatives, 15 and 16
5(6)-(N-Propargyl)amidofluorescein (15)

5(6)-Carboxyfluorescein (13; 1.13 g, 3 mmol) was first dissolved in 10 mL of THF followed by the slow addition of a 10-mL THF solution containing NHS (0.414 g, 3.6 mmol) and N,N'-dicyclohexylcarbodiimide (DCC, 0.70 g, 3.6 mmol). The resulting reaction mixture was stirred at rt for 2 h, concentrated under reduced pressure, and resuspended in pentane (5 L) to precipitate the orange-red-colored 5(6)-carboxyfluorescein N-hydroxysuccinimide ester (14; 0.145 g, 0.3 mmol). Without further purification, the acquired 14 was dissolved in 10 mL THF, followed by the addition of propargylamine (9; 39 µL, 0.6 mmol) and Et$_3$N (45 µL, 0.32 mmol) to initiate the reaction at rt for 3 h. The final reaction mixture was concentrated under reduced pressure, redissolved in EA (10 mL) and sequentially extracted with 1 N HCl, water and saturated NaCl. The afforded organic phase was dried over Na$_2$SO$_4$ and concentrated under reduced pressure to give 15 (0.08 g, 59%).

Compound 15: $^1$H NMR (400 MHz) (CD$_3$OD) δ: 8.01 (2H, s), 7.68 (1H, s), 7.33 (2H, dd), 6.58-6.57 (4H, m), 4.13 (2H, d), 2.59 (1H, t). $^{13}$C NMR (100.67 MHz) (CD$_3$OD) δ: 181.4, 160.5, 135.7, 132.3, 131.2, 130.6, 129.7, 129.2, 129.0, 123.7, 113.6, 72.2, 34.8. HRMS (ESI) calculated for C$_{24}$H$_{15}$NO$_6$, [M+Na]$^+$ 436.0797 (calculated), 436.0795 (found).

5(6)-[N-(5-azido-N'-ethylpentamido)]amidofluorescein (16)

Synthesis of 16 began with the crude 14 which was synthesized as described above and also used without further workup. A reaction mixture for 16 synthesis was prepared by dissolving crude 14 (260 mg, 0.55 mmol), 7 (0.98 mg, 0.58 mmol) and Et$_3$N (82 µL, 0.58 mmol) in a 6-mL DCM/DMF (5:1) solution while stirring at rt for 4 h. The final reaction mixture was concentrated under reduced pressure, redissolved in DCM (20 mL) and sequentially extracted with 1 N HCl, water and saturated NaCl. The resulting organic phase was dried over Na$_2$SO$_4$ and concentrated under reduced pressure to give 16 (0.08 g, 61%).

Compound 16: $^1$H NMR (400 MHz) (CD$_3$OD) δ: 8.47 (s, 1H), 8.11 (s, 1H), 7.63 (s, 1H), 7.32 (d, 1H), 6.69 (t, 4H), 6.60 (d, 1H), 6.58 (t, 2H), 6.56 (d, 1H), 4.17-4.04 (m, 2H), 2.35 (t, 2H), 2.27-2.22 (m, 2H), 1.70-1.56 (m, 2H). $^{13}$C NMR (100.67 MHz) (CD$_3$OD) δ: 103.8, 71.1, 66.5, 64.0, 52.1, 36.5, 34.9, 33.1, 30.8, 29.4, 26.7, 26.0. HRMS (ESI) calculated for C$_{28}$H$_{25}$N$_5$O$_7$, [M+Na]$^+$ 566.16462 (calculated), 566.16482 (found).

EXAMPLE 7

Synthesis of 6-propynoylamino-hexanoic acid 2,5-dioxopyrrolidin-1-yl ester (19)

-continued

Propiolic acid (17; 98.4 L, 1.6 mmol) was activated in an EDC (0.33 g, 1.6 mmol)-dissolved DMF solution (2 mL) at 0° C. while stirring for 15 min, followed by the addition of a 6-aminohexanoic acid (0.212 g, 1.61 mmol)-containing 1 M $Na_2CO_3$/DMF mixture (1 M $Na_2CO_3$/DMF=1:2; 3 mL) and reacting at rt for 3 h. The final reaction mixture was diluted with DCM, extracted with water twice and sat. NaCl once. The resulting organic phase was dried over $Na_2SO_4$ and concentrated under reduced pressure to give light orange-colored oily crude 18 (0.183 g, 1 mmol). Without further purification, the obtained 18 was dissolved in a DCM solution (5 mL) containing EDC (0.24 g, 1.2 mmol), followed by the addition of NHS (0.18 g, 1.2 mmol) and reaction at rt while stirring for 12 h. The final reaction mixture was diluted with DCM, extracted with water twice and saturated NaCl once. The afforded organic phase was again dried over $Na_2SO_4$ and concentrated under reduced pressure to obtain the golden-colored 19 (0.31 g, 82%).

Compound 19: $^1$H NMR (400 MHz) ($D_2O$) δ: 3.11 (t, 2H), 3.08-2.98 (m, 4H), 2.79 (s, 4H), 2.69 (s, 1H), 1.84-1.77 (m, 2H), 0.98 (t, 2H). $^{13}$C NMR (100.67 MHz) ($D_2O$) δ: 176.7, 174.5, 160.7, 55.4, 42.8, 36.5, 35.1, 25.5, 25.3, 25.1, 14.5. HRMS (ESI) calculated for $C_{13}H_{16}N_2O_5$, $[M+Na]^+$ 303.09514 (calculated), 303.09503 (found).

EXAMPLE 8

Nucleic Acid Preparation and Radio-Labeling

The single-stranded 3' primer DNA (SEQ ID NO. 3, 5'-TACCCCTTGGGGATACCACC-3') was purchased from Purigo Biotech, Inc., Taiwan and purified using 20% urea-PAGE. The TW17$_{1-17}$ RNA (SEQ ID NO. 4, 5'-GGGAUC-GUCAGUGCAUU-3'), which is the first 17 nucleotides in the TW17 RNA, was purchased from Bioneer (Daejeon, South Korea) and used without purification. Both the 3' primer DNA and the TW17$_{1-17}$ RNA were $^{32}$P-labeled at the 5'-end.

EXAMPLE 10

Modifications of Nucleic Acids with Azides and Alkynes
DNA

As prepared in N-hydroxysuccimide esters, either azides 6 or alkynes (9 and 19) were covalently linked to the ethylenediamine-modified 3' primer DNA by the amidation reaction reported previously (T.-P. Wang et al., Bioconjugate Chem., 2012, 23, 2417-2433). The ethylenediamine-conjugated 3' primer DNA was synthesized according to the optimized two-step phosphoramidation reaction of DNA in which ethylenediamine was the nucleophile in the reaction. Acquired DNA conjugates were purified by ethanol precipitation and analyzed using 20% urea-PAGE.

RNA

Similarly, N-hydroxysuccimide esters of either azides (6) or alkynes (9 and 19) were coupled to the cystamine-modified TW17$_{1-17}$ RNA by the same amidation reaction for DNA modifications indicated above. (T.-P. Wang et al., Bioconjugate Chem., 2012, 23, 2417-2433). The cystamine-conjugated TW17$_{1-17}$ RNA was also prepared by the optimized two-step phosphoramidation reaction of RNA in which cystamine served as the nucleophile in the reaction (T.-P. Wang et al., Bioconjugate Chem., 2010, 21, 1642-1655). Acquired RNA conjugates were again purified by ethanol precipitation and analyzed using 20% urea-PAGE.

EXAMPLE 10

Copper-Catalyzed 1,3-Dipolar Azide-Alkyne Cycloaddition for Nucleic Acid Modifications Nucleic acids were modified with appropriate substrates in the CuAAC reaction, and the best yield was attained. The acquired optimal CuAAC reactions are briefly stated below. Either azido- or alkynyl-modified DNA/RNA (80 pmol) and corresponding alkynyl- or azido-containing molecules (1.6 nmol) were dissolved in 8.85 μL phosphate buffer (100 mM potassium phosphate, pH 7.0), followed by the addition of a $CuSO_4$-THPTA premix solution (0.15 μL; prepared by mixing one part of 20 mM $CuSO_4$ in water and two parts of 50 mM THPTA in water), 0.5 μL of 100 mM aminoguanidine, and 0.5 μL of 100 mM fresh-prepared sodium ascrobate in sequence to obtain the final reaction mixture of 10 μL. After the reaction at rt for 1 h, the reaction products were purified by ethanol precipitation and analyzed using 20% urea-PAGE.

In addition, the optimal CuAAC reaction was scaled up ten times to more efficiently synthesize enough quantities of the Tat peptide-3' primer DNA conjugate (a POC) for bioactivity studies of the POC in human A549 cells. The scaled-up CuAAC reaction (10×) generally gave a triazole product yield similar to that of the optimal CuAAC reaction (1×).

EXAMPLE 11

Copper-Free Strain-Promoted 1,3-Dipolar Azide-Alkyne Cycloaddition for the Modification of Azido Nucleic Acids with the Cyclooctyne Substrate The azido nucleic acids were modified with the cyclooctyne Alkyne MegaStokes dye 608 based on Winz et al. (M.-L. Winz et al., Nucleic Acids Res., 2012, 40, e78) as described below. The azide-conjugated DNA/RNA (80 pmol) was dissolved in 76 μL of phosphate buffer (50 mM potassium phosphate, pH 7.0) to obtain an 1 μM nucleic acid solution. The SPAAC reaction was initiated by adding in 0.4 μL of Alkyne MegaStokes dye 608 (10 mM in DMSO) and proceeded at 35° C. for 2 h. The final reaction products were purified by ethanol precipitation and analyzed using 20% urea-PAGE.

EXAMPLE 12

Cytotoxicity by MTT Assay

The cytotoxicity of inoculates was determined by MTT assays against A549 cells. In brief, A549 cells were seeded in 96-well tissue culture plates at a density of 5×10$^3$/well in a medium containing 10% FBS before treating inoculates. The cytotoxicity of the inoculates was evaluated by determining cell viability after 24 h of incubation with various concentrations of inoculates (1-10 µM). The number of viable cells was acquired by estimating their mitochondrial reductase activity using the tetrazolium-based colorimetric method (MTT conversion test).

EXAMPLE 13

Flow Cytometry Analysis of Cellular Uptake

In order to observe the cellular uptake efficiency of the inoculates, A549 cells were seeded in 6-well culture plates at a density of $2\times10^5$/well in a medium containing 10% FBS for 24 h. The medium containing 5 µM concentration of inoculates were added to cells. After 24 h of incubation, cells were washed, trypsinized, centrifuged, and resuspended in 1 mL of cold PBS, and then analyzed using the flow cytometer. The fluorescein-labeled inoculates (peptide, DNA and POC) used in flow cytometry and confocal laser scanning microscopy were prepared according to published methods (T.-P. Wang et al., *Bioconjugate Chem.*, 2012, 23, 2417-2433).

EXAMPLE 14

Confocal Laser Scanning Microscopy (CLSM)

The intracellular delivery of inoculates was observed using CLSM. A549 cells were seeded at a density of $1.0\times10^5$/well in 12-well plates containing one glass coverslip/well in RPMI supplemented with 10% FBS, and then incubated for 24 h. Each inoculate of 5 µM was added to cells for 24 h at 37° C. After incubation, the inoculate-containing medium was removed and washed gently with 1 mL of 0.1 M PBS at pH 7.4. The cell nuclei was then stained with 5 µg/mL Hoechst 33342 (Invitrogen, Carlsbad, Calif.) for 30 min. The cells on the coverslips were washed 3 times with 0.1 M PBS and mounted with a fluorescent mounting medium on glass slides. Cell imaging was obtained using CLSM (Fv 1000; Olympus, Tokyo, Japan) and analyzed using Olympus CLSM software.

EXAMPLE 15

Optimal Azide-Alkyne Cycloaddition for Universal Modifications of Nucleic Acids

The optimal CuAAC reactions for azide- and alkyne-modified DNA/RNA derived from the two-step phosphoramidation reactions were effectively developed with all the required reagents. The inventors first determined that 6c and 6d were better electrophiles to react with amino-nucleic acids and provided higher yields of azide-modified nucleic acids. For the synthesis of alkyne-modified DNA/RNA, the commercially available propargylamine (9) was first used as the substrate for nucleic acid modifications. The 9-modified DNA/RNA, however, resulted in sluggish CuAAC reactions with low yield.

Figure 3:
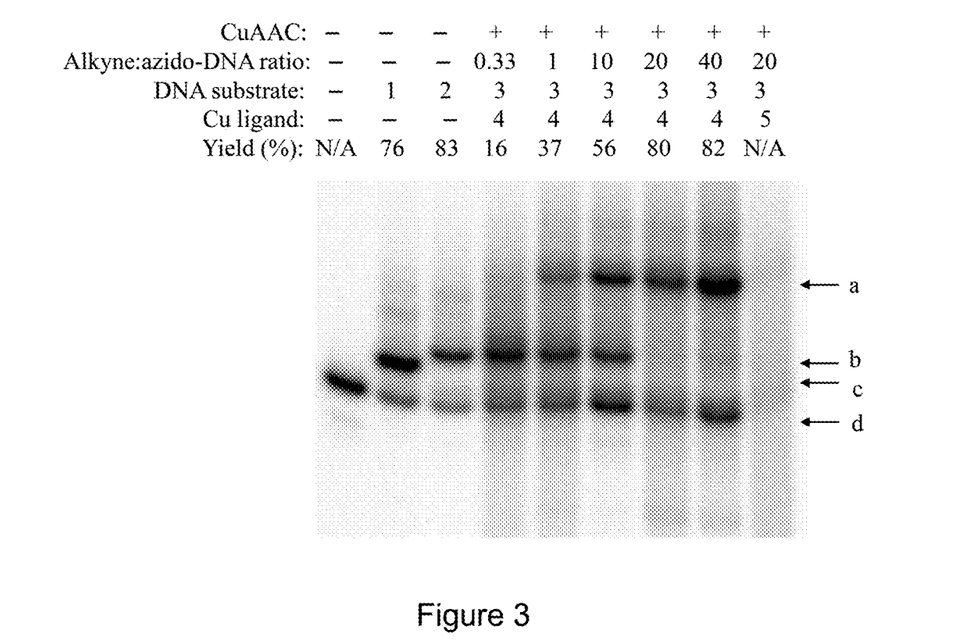
FIG. 3 is gel electrophoretic results showing that the studied DNA was the 3' primer DNA and was labeled with 32-P at the 5' end before the reactions. The reaction products were analyzed by 20% urea-PAGE and visualized by an Amersham Typhoon PhosphorImager. 1, ethylenediamine; 2, ethylenediamine+6d; 3, ethylenediamine+6d+10; 4, tris (3-hydroxypropyltriazolylmethyl)amine (THPTA); 5, tris (benzimidazol-2-ylmethyl)amine (NTB); a, the CuAAC reaction product between the azido 3' primer DNA and 10; b, the 6d-ethylenediamine-3' primer DNA conjugate; c, the ethylenediamine-modified 3' primer DNA; and d, the 3' primer DNA.

The inventors envisioned that the reaction yield could be improved by moving the alkynyl group away from the nucleic acids and introducing an electron-withdrawing group adjacent to the alkynyl group. Indeed, when substituting 19 for 9 in nucleic acid conjugates, the CuAAC reactions provided far better yield. The inventors then systematically surveyed the effects of nucleic acid concentration, the concentrations of 6c/6d and 19, copper concentration, THPTA concentration, reaction pH, the azide:alkyne ratio (FIG. 3), and the Cu:THPTA ratio to obtain the optimal reaction conditions for the conjugation of azide-/alkyne-modified nucleic acids with corresponding alkyne/azide substrates.

Figure 1A:
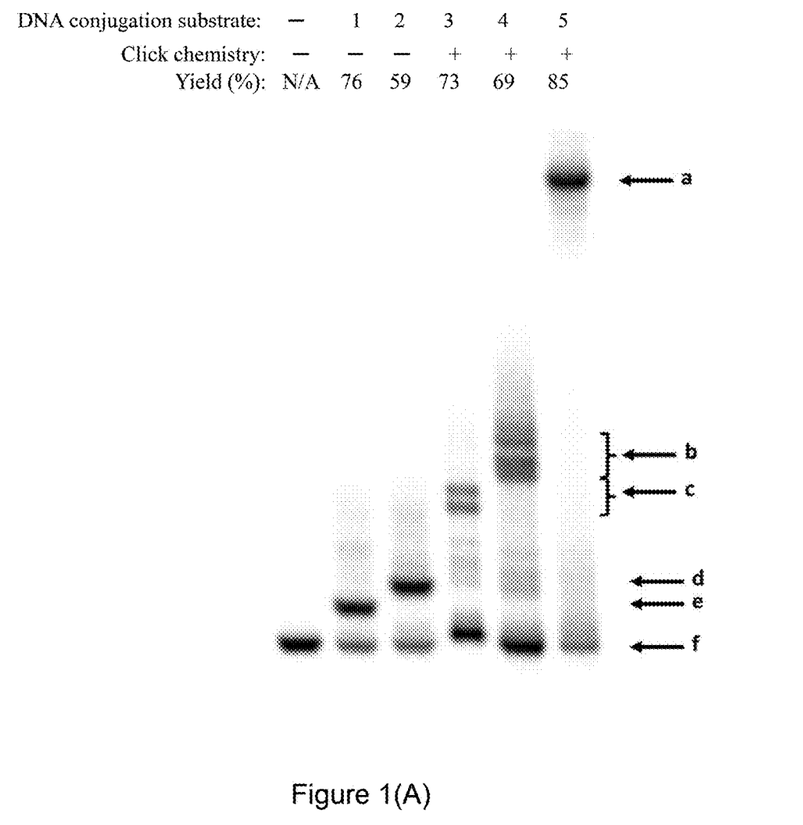
FIGS. 1(A) and 1(B) are gel electrophoretic results showing azide-alkyne cycloaddition for conjugations of the $^{32}$P-labeled azide-modified (A) 3' primer DNA and (B) 17-mer RNA with alkynyl-containing substrates. Lanes in FIG. 1(A): 1, ethylenediamine; 2, ethylenediamine+6d; 3, ethylenediamine+6d+Alkyne MegaStokes dye 608; 4, ethylenediamine+6d+15; and 5, ethylenediamine+6d+the alkynyl Tat peptide. Lanes in FIG. 1(B): 6, cystamine; 7, cystamine+6c; and 8, cystamine+6c+15 Labels in FIG. 1(A): a, the azido-3' primer DNA-alkynyl Tat peptide conjugate prepared by the CuAAC reaction; b, the azido-3' primer DNA-15 conjugate prepared by the CuAAC reaction; c, the azido-3' primer DNA-Alkyne MegaStokes dye 608 conjugate prepared by the SPAAC reaction; d, the 3' primer DNA-ethylenediamine-6d conjugate; e, the 3' primer DNA-ethylenediamine conjugate; and f, the 3' primer DNA. Labels in FIG. 1(B): g, the azido-17-mer RNA-10 conjugate prepared by the CuAAC reaction; h, the 17-mer RNA-cystamine-6c conjugate; i, the 17-mer RNA-cystamine conjugate; and j, the 17-mer RNA.
Figure 1B:
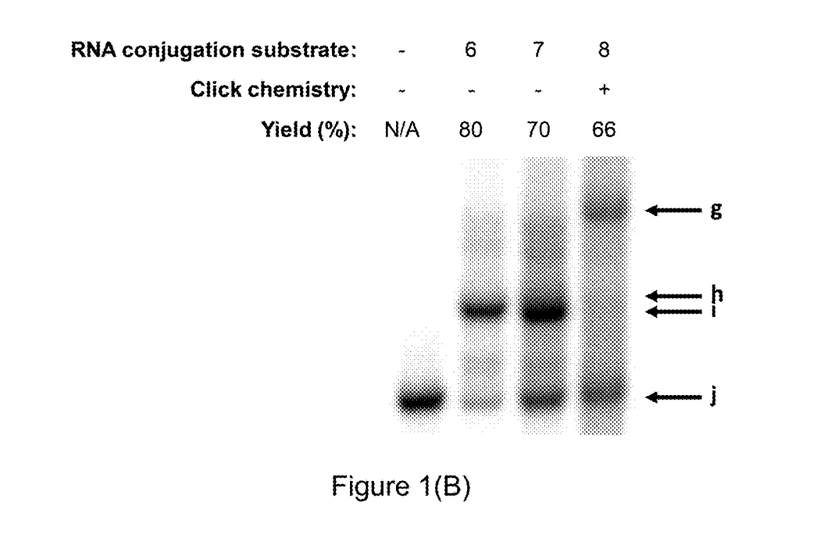

Please refer to FIGS. 1(A) and 1(B), azide-alkyne cycloaddition for conjugations of the $^{32}$P-labeled azide-modified (A) 3' primer DNA and (B) 17-mer RNA with alkynyl-containing substrates.

Figure 2A:
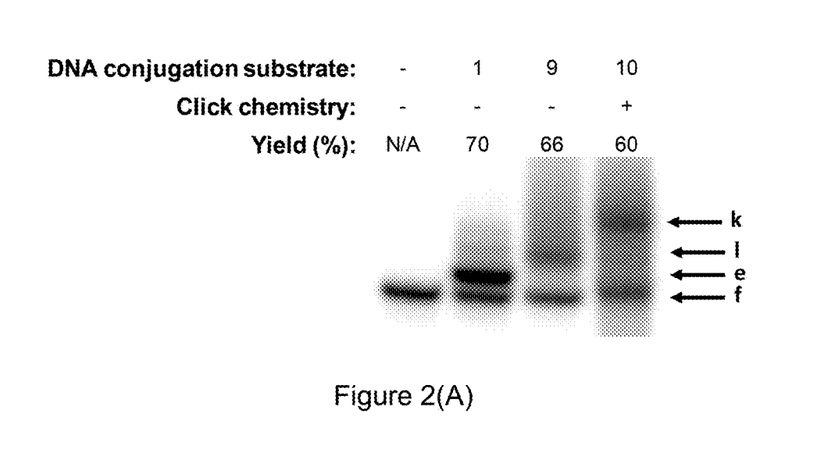
Figure 2B:
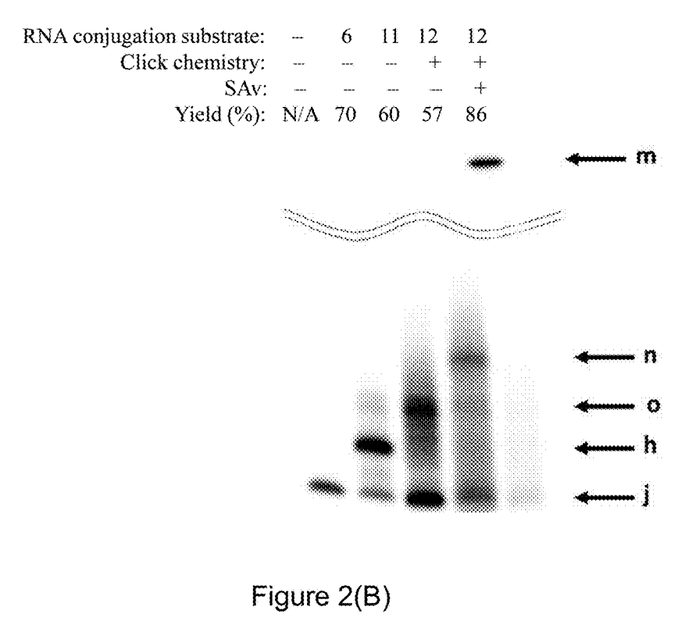

The optimal CuAAC reactions were successfully exploited to synthesize various nucleic acid conjugates. For instance, the azide-modified 3' primer DNA was effectively conjugated with several alkynyl-containing substrates [referring to FIG. 1(A) and steps (a) through (c) in the first embodiment above]. Similar results were acquired by using azide-modified RNA in the optimal CuAAC reactions [FIG. 1(B)]. Moreover, the alkyne-modified 3' primer DNA was also effectively conjugated with azido-containing substrates by the other optimized CuAAC reaction [referring to FIG. 2(A) and steps (a) through (c) in the second embodiment above]. Again, a similar high yield was observed in the optimized CuAAC reaction when azides were reacted with the alkyne-modified 17-mer RNA [FIG. 2(B)]. The presence of biotin and fluorescein moieties in the CuAAC triazole products was confirmed by streptavidin (SAv) gel-shift analysis and fluorescence imaging after electrophoresis [FIG. 2(B)]. In addition, the modified nucleic acids were gel-purified and analyzed by matrix-assisted laser desorption ionization-time of flight mass spectrometry (MALDI-TOF MS) to demonstrate the production of the expected DNA and RNA conjugates.

The inventors again employed the two-step phosphoramidation reactions to easily synthesize azido-containing nucleic acids which could react with cyclooctynes in the SPAAC reaction (referring to the first embodiment above). Congruent with expectations, the cyclooctyne Alkyne Mega-Stokes dye 608 [DNA conjugation substrate 3 in FIG. 1(A)] was smoothly labelled to the azide-modified 3' primer DNA without incurring detectable DNA degradation. Moreover, the identity of the gel-purified MegaStokes dye 608-modified DNA was affirmed by MALDI-TOF MS analysis. The results clearly show the reactivities of phosphoramidation reaction-derived azido-containing nucleic acids in the CuAAC and SPAAC reactions to provide the desired modified nucleic acids with good yields.

EXAMPLE 16

CuAAC for POC Synthesis

The inventors employed the optimized CuAAC reaction to more effectively synthesize POCs [referring to steps (a) through (c) of the third embodiment above] and demonstrate the cell-penetrating ability of the acquired POCs. Click chemistry has been applied for POC synthesis. However, past POC synthesis studies depended on solid-phase phosphoramidite chemistry to afford alkynyl- or amino-containing oligonucleotides and the CuAAC reaction to obtain POCs. Intriguingly, these synthesized POCs were never administered to biological systems nor did they demonstrate cell-penetrating activity. Here the inventors successfully exploited the optimized CuAAC reaction and conjugated the azide-modified FITC-labelled 3' primer DNA with an alkynyl-containing Tat peptide [DNA conjugation substrate 5 in FIG. 1(A)] with an excellent yield [FIG. 1(A)].

Figure 4:
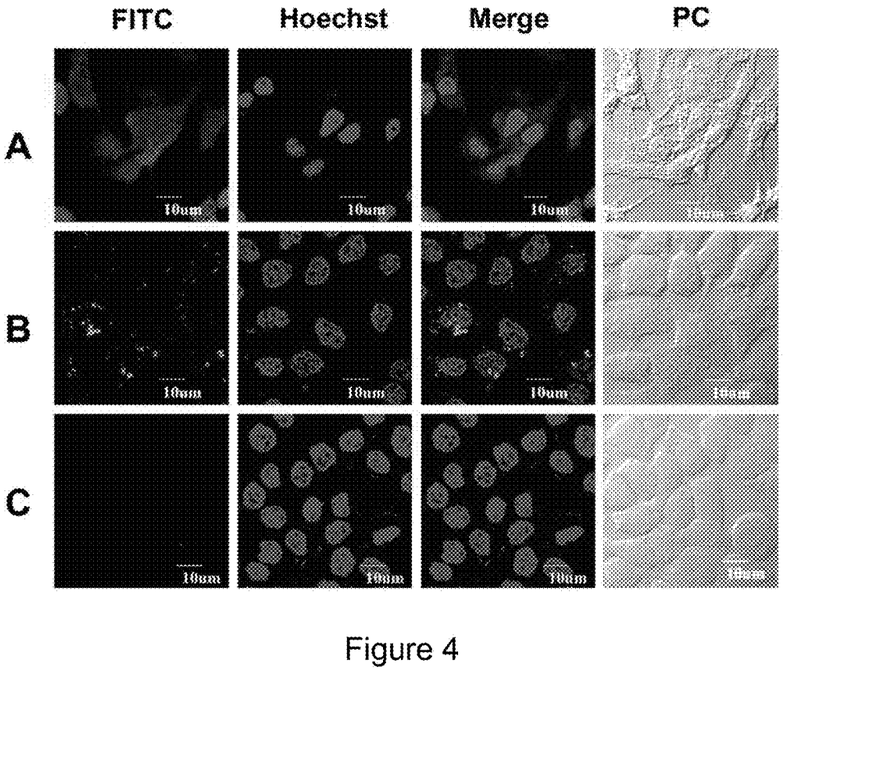
FIG. 4 is a set of confocal laser scanning microscopic images showing the combination of phosphoramidation and CuAAC reactions to synthesize POCs successfully taken up by human A549 cells. A, the alkynyl Tat peptide-azido 3' primer DNA conjugate (the POC) with fluorescein isothiocyanate (FITC) labelled to the DNA; B, the FITC-labelled alkynyl Tat peptide; and C, the FITC-labelled 3' primer DNA. PC, phase contrast.

Please refer to FIG. 4, wherein the inventors further demonstrate translocation of the EDTA-treated POC into human A549 cells after inoculation by confocal laser scan- ning microscopy (FIG. 4) even though the deformation of A549 cells was visible (PC in row A of FIG. 4).

EMBODIMENTS

Embodiment 1: A method for modifying an oligonucleotide, comprising:
(a) conjugating $H_2N(CH_2)_nNH_2$ to the 5' end of the oligonucleotide to form a conjugated product;
(b) amidating the free $-NH_2$ group of the conjugated product with $R_1-N_3$; and
(c) reacting the terminal $-N_3$ group with one of $HC\equiv C-R_2$ and a cycloalkyne, wherein n is an integer from 2 to 6, $R_1$ is a first substituent, and $R_2$ is a second substituent.

Embodiment 2 is a method as described in Embodiment 1, wherein the first substituent and the second substituent are carbonaceous substituents.

Embodiment 3 is a method as described in Embodiment 1, wherein $R_1-N_3$ is $HC\equiv C-R_2$ is one selected from a group consisting of an alkynyl derivative of biotin, an alkynyl derivative of fluorescein, and an alkynyl carboxylic acid succinimidyl ester; $R_3$ is $-(CH_2)_m-$, and m is an integer from 2 to 5.

Embodiment 4 is a method as described in Embodiment 1, wherein $R_2$ is a cell-penetrating peptide.

Embodiment 5 is a method as described in Embodiment 4, wherein the cell-penetrating peptide is a trans-activating transcriptional activator (TAT) peptide.

Embodiment 6 is a method as described in Embodiment 3, wherein the alkynyl derivative of biotin is Embodiment 7 is a method as described in Embodiment 3, wherein the alkynyl derivative of fluorescein is Embodiment 8 is a method as described in Embodiment 3, wherein the alkynyl carboxylic acid succinimidyl ester is Embodiment 9 is a method as described in Embodiment 1, wherein the cycloalkyne is 1-{3-{[4-(2-cyclooctyn-1-ylmethyl)benzoyl]amino}propyl}-4-{2-[4-(dimethylamino)phenyl]ethenyl}pyridinium hexafluorophosphate.

Embodiment 10 is a method as described in Embodiment 1, wherein the reacting step is one of a copper-catalyzed azide-alkyne cycloaddition reaction and a strain-promoted azide-alkyne cycloaddition reaction.

Embodiment 11 is a method as described in Embodiment 1, wherein the oligonucleotide is an antisense oligonucleotide, siRNA, miRNA or a splice switching oligonucleotide.

Embodiment 12: A method for modifying an oligonucleotide, comprising:
(a) conjugating $H_2N(CH_2)_nNH_2$ to the 5' end of the oligonucleotide to form a conjugated product;
(b) amidating a free $-NH_2$ group of the conjugated product with $R_1-C\equiv CH$; and
(c) reacting the alkyne group with $R_4-N_3$, wherein n is an integer from 2 to 6, $R_1-C\equiv CH$ is $R_3$ is $-(CH_2)_m-$, m is an integer from 2 to 5, and $R_4-N_3$ is one selected from a group consisting of an azido derivative of biotin and an azido derivative of fluorescein.

Embodiment 13 is a method as described in Embodiment 12, wherein the azido derivative of biotin is Embodiment 14 is a method as described in Embodiment 12, wherein the azido derivative of fluorescein is Embodiment 15 is a method as described in Embodiment 12, wherein the reacting step is one of a copper-catalyzed azide-alkyne cycloaddition reaction and a strain-promoted azide-alkyne cycloaddition reaction.

Embodiment 16: A method for modifying a nucleic acid, comprising:
(a) conjugating $H_2N(CH_2)_nNH_2$ to the 5' end of the nucleic acid to form a conjugated product;
(b) reacting a free —$NH_2$ group of the conjugated product with R—$N_3$ and R'—C≡CH to form a nucleic acid compound, wherein n is an integer from 2 to 6, R is a substituent in azide, and R' is a substituent in alkyne.

Embodiment 17 is a method as described in Embodiment 16, wherein R—$N_3$ is one being selected from a group consisting of Embodiment 18 is a method as described in Embodiment 17, wherein $R_5$ is —$(CH_2)_m$—, and m is an integer from 2 to 5.

Embodiment 19 is a method as described in Embodiment 16, wherein R'—C≡CH is one being selected from a group consisting of Embodiment 20 is a method as described in Embodiment 19, wherein $R_6$ is —$(CH_2)_m$—, and m is an integer from 2 to 5.

Embodiment 21 is a method as described in Embodiment 16, wherein R' is a cell-penetrating peptide.

Embodiment 22 is a method as described in Embodiment 20, wherein the cell-penetrating peptide is a trans-activating transcriptional activator (TAT) peptide.

Embodiment 23 is a method as described in Embodiment 16, wherein the nucleic acid is a single-stranded or a double-stranded DNA or RNA, a nucleic acid analog or chimera thereof with DNA and/or RNA or an enzymatically modified PCR product.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A method for modifying a nucleic acid molecule, comprising:

(a) monophosphoramidating $H_2N(CH_2)_nNH_2$ to the 5' end of the nucleic acid to form a conjugated product, wherein n is an integer from 2 to 6, and the conjugated product has a formula of:

(b) amidating the free $-NH_2$ group of the conjugated product by contacting with $R^1-N_3$, wherein $R^1-N_3$ is $R^3$ is $-(CH_2)_m-$, and m is an integer from 2 to 5; and (c) reacting the terminal $-N_3$ group with a cyclooctyne.

2. The method of claim 1, wherein the cyclooctyne is 1-{3-{[4-(2-cyclooctyn-1-ylmethyl)benzoyl]amino}propyl}-4-{2-[4-(dimethylamino)phenyl]ethenyl}pyridinium hexafluorophosphate.

3. The method of claim 1, wherein the reacting step is a strain-promoted azide-alkyne cycloaddition reaction.

* * * * *

SEQUENCE LISTING

<160> NUMBER OF SEQ ID NOS: 4

<210> SEQ ID NO 1
<211> LENGTH: 10
<212> TYPE: PRT
<213> ORGANISM: artificial sequence
<220> FEATURE:
<223> OTHER INFORMATION: Artificially Synthesized Amino Acid Sequence

<400> SEQUENCE: 1

Gly Arg Lys Lys Arg Arg Gln Arg Arg Arg
1               5                   10

```
<210> SEQ ID NO 2
<211> LENGTH: 87
<212> TYPE: RNA
<213> ORGANISM: artificial sequence
<220> FEATURE:
<223> OTHER INFORMATION: Artificially Synthesized RNA Sequence

<400> SEQUENCE: 2
gggaucguca gugcauugag aagugcagug ucuugcgcug gguucgagcg guccguggug    60
cuggcccggu gguaucccca aggggua                                       87

<210> SEQ ID NO 3
<211> LENGTH: 20
<212> TYPE: DNA
<213> ORGANISM: artificial sequence
<220> FEATURE:
<223> OTHER INFORMATION: Artificially Synthesized DNA Sequence

<400> SEQUENCE: 3
taccccttgg ggataccacc                                               20

<210> SEQ ID NO 4
<211> LENGTH: 17
<212> TYPE: RNA
<213> ORGANISM: artificial sequence
<220> FEATURE:
<223> OTHER INFORMATION: Artificially Synthesized RNA Sequence

<400> SEQUENCE: 4
gggaucguca gugcauu                                                  17
```